(12) United States Patent
Kraft et al.

(10) Patent No.: US 11,878,146 B2
(45) Date of Patent: Jan. 23, 2024

(54) MEASUREMENT PROBE FOR AN INJECTION DEVICE

(71) Applicant: SANOFI, Paris (FR)

(72) Inventors: Torsten Kraft, Frankfurt am Main (DE); Alex Meier, Frankfurt am Main (DE)

(73) Assignee: Sanofi, Paris (FR)

( * ) Notice: Subject to any disclaimer, the term of this patent is extended or adjusted under 35 U.S.C. 154(b) by 708 days.

(21) Appl. No.: 17/052,244

(22) PCT Filed: Apr. 26, 2019

(86) PCT No.: PCT/EP2019/060708
§ 371 (c)(1),
(2) Date: Nov. 2, 2020

(87) PCT Pub. No.: WO2019/211180
PCT Pub. Date: Nov. 7, 2019

(65) Prior Publication Data
US 2021/0170105 A1  Jun. 10, 2021

(30) Foreign Application Priority Data

May 4, 2018 (EP) .................................... 18305560

(51) Int. Cl.
*A61M 5/24* (2006.01)
(52) U.S. Cl.
CPC ....... *A61M 5/24* (2013.01); *A61M 2005/2492* (2013.01); *A61M 2205/332* (2013.01)
(58) Field of Classification Search
CPC .............. A61M 2205/332; A61M 5/24; A61M 2005/2433; G01B 21/32
See application file for complete search history.

(56) References Cited

U.S. PATENT DOCUMENTS

| 3,811,193 A | 5/1974 | Rapp |
| 4,577,629 A | 3/1986 | Martinez |
| 4,873,990 A | 10/1989 | Holmes et al. |

FOREIGN PATENT DOCUMENTS

| CN | 104968380 | 10/2015 |
| CN | 106802132 | 6/2017 |

(Continued)

OTHER PUBLICATIONS

PCT International Preliminary Report on Patentability in International Application No. PCT/EP2019/060708, dated Nov. 10, 2020, 5 pages.

(Continued)

*Primary Examiner* — Deanna K Hall
(74) *Attorney, Agent, or Firm* — Fish & Richardson P.C.

(57) ABSTRACT

The present disclosure relates to a measurement probe for measuring a mechanical load. The measurement probe includes: an elongated body comprising a tubular portion configured for insertion into a cartridge holder of an injection device, a sensor tab arranged on or integrated into the elongated body, wherein the sensor tab comprises an outside surface portion, an inside surface portion and an outer abutment section, wherein the outer abutment section is configured to abut with an inside of a sidewall of the cartridge holder and wherein the sensor tab is deformable in a radial direction, a sensor element mechanically connected to the at least one sensor tab and configured to measure a deformation of the at least one sensor tab.

20 Claims, 5 Drawing Sheets

(56) References Cited

FOREIGN PATENT DOCUMENTS

| | | |
|---|---|---|
| EP | 2957308 | 12/2015 |
| WO | WO 2014/118107 | 8/2014 |
| WO | WO 2017/191177 | 11/2017 |

OTHER PUBLICATIONS

PCT International Search Report in International Application No. PCT/EP2019/060708, dated Jun. 21, 2019, 7 pages.

MEASUREMENT PROBE FOR AN INJECTION DEVICE

CROSS REFERENCE TO RELATED APPLICATIONS

The present application is the national stage entry of International Patent Application No. PCT/EP2019/060708, filed on Apr. 26, 2019, and claims priority to Application No. EP 18305560.7, filed on May 4, 2018, the disclosures of which are incorporated herein by reference.

TECHNICAL FIELD

The present disclosure relates to a measuring probe for measuring a mechanical load, in particular for measuring of a mechanical load present on a medicament container in the course of assembly of an injection device. In another aspect the disclosure relates to a measurement system comprising an injection device and comprising a measurement probe located inside the injection device for measuring a mechanical load usually acting on a medicament cartridge in the course of assembly of the injection device.

In a further aspect the disclosure relates to a method of measuring a mechanical load acting on a measurement probe or acting on an identically shaped medicament container or cartridge in the course of assembly of an injection device equipped with such a measurement probe or medicament container.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, such as pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

Typically, such devices comprise a housing or a particular cartridge holder, adapted to receive a medicament container, e.g. in form of a cartridge at least partially filled with the medicament to be expelled. The device further comprises a drive mechanism, usually having a displaceable plunger or piston rod to operably engage with a bung or piston of the medicament container or cartridge. By means of the drive mechanism and its piston rod, the bung or piston of the cartridge is displaceable in a distal or dispensing direction and may therefore expel a predefined amount of the medicament via a piercing assembly, e.g. in form of an injection needle, connected to or releasably connectable with an outlet end of the medicament container. With reusable drug delivery devices an empty cartridge is replaceable by a filled one. In contrast to that, drug delivery devices of disposable type are to be entirely discarded when the medicament in the cartridge has been dispensed or used-up.

With some injection devices, such as with handheld pen-type injectors a medicament container is placed inside a housing of the injection device. The housing is made from two parts which are locked together in the course of a final assembly of the injection device. A proximal housing component, typically denoted as body, is configured to accommodate a drive mechanism having a plunger or piston rod to exert a distally directed pressure to a bung of a cartridge. A distal housing component, typically denoted as a cartridge holder, is configured to accommodate a cartridge filled with the medicament. The cartridge typically comprises a tubular barrel filled with the medicament and sealed in proximal direction, hence towards the drive mechanism by a bung axially displaceably arranged inside the barrel.

During the assembly process of such an injection devices the medicament container or cartridge containing the injectable medicament is positioned and assembled inside the cartridge holder. The drive mechanism including at least the plunger or piston rod to operably engage is assembled inside the body, i.e. the proximal housing component. The cartridge holder with the cartridge assembled therein forms a cartridge holder preassembly whereas the body with the drive mechanism assembled therein forms or constitutes a body preassembly.

During a final step of assembly the cartridge holder preassembly and the body preassembly are assembled and connected together. For this a proximal end of the cartridge holder is fixed to a distal end of the body. Typically, cartridge holder and body comprise an insert portion and a correspondingly-shaped receptacle so that the proximal end of the cartridge holder and the distal end of the body are assembled in a nested or interleaved way. In a mutually overlapping section there are typically provided mutually corresponding fasteners, such as radially outwardly or radially inwardly extending mutually corresponding snap features on the insert portion and on in the correspondingly shaped receptacle. For instance an insert section of the cartridge holder may be provided with at least one or several recesses or through holes in a sidewall section that are configured to receive and to engage with at least one radially inwardly protruding latch element provided on an inside facing portion of a sidewall of the receptacle of the body, in which the insert section of the cartridge holder is located.

Such a clip connection based on protruding snap features and recesses or holes may be disadvantageous for a barrel of the cartridge made from a vitreous material. Typically, the cartridge firmly attached or assembled inside the cartridge holder may experience a non-negligible radially inwardly directed compression as the snap features of the receptacle of the body snap into correspondingly-shaped holes in the insert section of the cartridge holder. In order to establish such clip connections the sidewalls of the interleaved housing sections of cartridge holder and body are temporally subject to at least a marginal radial deformation. In practice it has turned out that such marginal or minor radial deformation of the cartridge holder or of its insert portion may cause significant stress to the glass cartridge assembled therein.

SUMMARY

In order to develop a function specific design of the housing of the injection device it is desirable to obtain not only qualitative but also quantitative information about a mechanical stress level applied on a medicament container or cartridge during the assembly process of the injection device. It is hence desirable to measure mechanical load acting on a cartridge during the assembly process of the injection device quantitatively. Such a measurement could offer a function specific design of the housing of the injection device in order to reduce mechanical load or mechanical stress applied to the medicament container or cartridge during assembly of the injection device.

In one aspect the disclosure relates to a measurement probe for measuring a mechanical load. The measurement probe comprises an elongated body comprising a tubular portion configured for insertion into a cartridge holder of an injection device. The entire elongated body is configured for insertion into a cartridge holder. Typically, the elongated body has the form and the shape of a medicament container filled with a liquid medicament, which medicament is configured to be dispensed or injected by the injection device. The measurement probe conforms to the outer shape of the medicament container or cartridge normally or usually to be inserted into the injection device and to be used with the injection device. In other words, the measurement probe may represent a dummy cartridge.

The measurement probe comprises at least one sensor tab arranged on or integrated into the elongated body. The at least one sensor tab comprises an outside surface portion, an inside surface portion and an outer abutment section. The outer abutment section is configured to abut with an inside of a sidewall of the cartridge holder when the measurement probe is arranged inside the cartridge holder. The at least one sensor tab is deformable in a radial direction. The measurement probe further comprises at least one sensor element that is mechanically connected to the at least one sensor tab. The at least one sensor element is configured to measure a deformation of the at least one sensor tab, typically during assembly of the injection device when the measurement probe is arranged inside the cartridge holder.

The radial direction is defined in view and with regards to the tubular portion of the elongated body. The tubular portion and the entire elongated body comprise a central axis defining an axial direction. The radial direction extends perpendicular to this central axis and in radial direction with regard to the tubular shape of the tubular portion of the elongated body.

The combination of the at least one sensor tab with the at least one sensor element enables a measurement of a geometric deformation of the at least one sensor tab in the course of assembly of the injection device. The sensor tab typically exhibits a well-defined deformability. The degree of geometric deformation of the at least one sensor tab may be unequivocally or unambiguously correlated to a force applied to the sensor tab in radial direction. In other words, the degree of radial deformation of the at least one sensor tab is a direct measure of a radial force acting on the sensor tab. The at least one sensor tab is particularly configured to measure a radially inwardly directed force effect acting on the sensor tab, typically in the course of assembly of the injection device.

The mechanical connection of the at least one sensor tab with the at least one sensor element provides generation of a measurement signal being indicative of the mechanical and geometric deformation of the sensor tab. The at least one sensor element is typically implemented electrically. The at least one sensor element is configured to generate or to modify at least one electrically measurable sensor signal in response to a mechanical or geometric deformation of the at least one sensor tab. With some examples even the at least one sensor element may be subject to geometric deformations that are directly measurable by the sensor element. Sensor signals generated by the at least one sensor element can be electronically processed, e.g. by a measurement circuit and/or by a microprocessor connected to the at least one sensor element in a signal transmitting way.

According to a further example the at least one sensor tab is elastically deformable. An elastically deformable sensor tab is reversibly geometrically deformable. In this way, the sensor tab can be used multiple times. The sensor tab exhibits a well-defined deformation behavior in response to a radial force effect acting on the sensor tab. The elastic module of the material of the sensor tab and/or the specific geometry of the sensor tab leads to a well-defined and geometric deformation of the sensor tab in response to a force effect. The measurable geometric deformation is then a direct, unequivocal and unambiguous measure for the force acting upon the at least one sensor tab.

According to a further example the at least one sensor tab is integrally formed with the elongated body. The elongated body and the at least one sensor tab may be made of a metal or a metal alloy. The sensor tab and/or the elongated body may therefore be rather robust.

Generally, the elongated body and the at least one sensor tab may also be made from a plastic material. The may comprise a unitary injection molded plastic component.

The unitary implementation of the at least one sensor tab and the elongated body is beneficial to provide a highly reproducible deformation behavior of the at least one sensor tab. This is of particular benefit, when the measurement probe does not only comprise one but a plurality of substantially identically shaped sensor tabs. Here, all sensor tabs may be integrally formed with the elongated body. In this way, they may exhibit substantially identical deformation properties in response to a mechanical load acting on the respective sensor tab. Otherwise and if the sensor tabs would be provided as separate pieces configured for connection to the elongated body, the specific connection of the sensor tabs to the body may have a significant influence on their mechanical deformation behavior.

According to a further example the at least one sensor tab is arranged at a proximal end of the body and protrudes proximally from the tubular portion. The at least one sensor tab, in particular its proximal end may coincide with a position in which the proximal end of a medicament container is located when correctly assembled inside the injection device. In this way, the at least one sensor tab is configured to measure a mechanical load applied from at least one of the housing components of the injection device to a proximal end of the cartridge when assembled inside the injection device. A sensor tab protruding proximally from the tubular portion further provides a well-defined mechanical deformation capability. In this way, the at least one sensor tab comprises a free end at its proximal end. It may thus provide a kind of a bending beam or bending bar. Even if the sensor tab can be made of a rather rigid and inflexible material the specific geometry of the at least one sensor tab protruding from the proximal end of the tubular portion may exhibit a well-defined quantitatively measurable deformation behavior even if the radial force acting upon the sensor tab can be comparatively low. In this way, the measurement precision and measurement sensitivity can be increased.

In a further example the outside surface portion of the at least one sensor tab is flush with an outside surface of the tubular portion as seen in longitudinal direction. Moreover, the outside surface portion of the at least one sensor tab may extend parallel to the outside surface of the tubular portion of the elongated body. In this way, the outside surface portion of the at least one sensor tab forms a proximal extension of the outside surface of the tubular portion. The outside surface portion and the at least one sensor tab typically conform to the outer shape of the tubular shaped cartridge normally to be inserted into the cartridge holder of the injection device.

The arrangement of the outer surface portion of the at least one sensor tab flush with the outside surface of the tubular portion is of particular benefit when the at least one sensor tab is integrally formed with the elongated body. Hence, the interface between the proximal end of the tubular portion and a distal end of the at least one sensor tab may be void of any radial protrusions or recesses. The flush arrangement and the parallel orientation of the entire outside surface portion of the at least one sensor tab with the outside surface of the tubular portion is beneficial in that the proximal end of the at least one sensor tab is located at the same radial position as the outside surface of the tubular portion.

With a further example the abutment section of the at least one sensor tab is located at a proximal end of the at least one sensor tab. The abutment section is typically located on the outside surface of that at least one sensor tab. In this way, the abutment section is configured to engage or to radially abut with the inside of the sidewall of the cartridge holder when the measurement probe is assembled inside the cartridge holder and when the cartridge holder is attached or assembled to the body of the injection device.

According to a further example the abutment section of the at least one sensor tab bulges outwardly from the outside surface portion. In this way, the abutment section conforms to the bulged portion at the very end of a vitreous body of a cartridge. Typically, vitreous barrels forming a medicament container or a medicament cartridge feature an enamel edge that is due to the manufacturing process of the vitreous barrel. Typically, vitreous barrels for medicament containers or cartridges feature such a bulged portion, which is rather susceptible to radially inwardly directed mechanical load in the course of assembly of the injection device. By providing the abutment section with a bulged portion protruding from the outside surface portion of the at least one sensor tab, the at least one sensor tab precisely imitates the geometric shape of an enamel edge or bulged portion at a proximal end of a vitreous barrel of a medicament container or cartridge. In this way, mechanical load acting especially on the enamel edge or bulged portion at a proximal end of the vitreous barrel of the medicament container can be precisely measured and/or monitored by the measurement probe.

In a further example the at least one sensor tab comprises a narrowing radial thickness towards the proximal end. In other words, the at least one sensor tab tapers towards the proximal end. As seen in longitudinal and radial direction, the at least one sensor tab comprises a decreasing wall thickness towards the proximal end of the elongated body. Such a reduced thickness is of particular benefit to exhibit a well-defined geometric deformation in response to a mechanical load acting on the proximal end of the sensor tab, e.g. on the abutment section of the at least one sensor tab.

With a further example the inside surface portion of the at least one sensor tab is inclined inwardly towards a distal end of the body with regard to a central axis of the body. This particularly applies where the at least one sensor tab comprises a narrowing radial thickness towards the proximal end. Here, the outside surface portion of the at least one tab is flush and parallel with the outside surface of the tubular portion. The tapered profile is exclusively due to the inclination of the inside surface portion of the at least one sensor tab. In this way a proximal end of the sensor tab comprises a radial thickness at a proximal end that is smaller than a distal radial thickness at a distal end of the at least one sensor tab. The distal end of the at least one sensor tab is connected to or integrally formed with the tubular portion of the elongated body. In this way, the elasticity of the at least one sensor tab gradually increases towards the proximal end.

According to a further example the at least one sensor element is fixed on the inside surface portion of the at least one sensor tab. The at least one sensor element may cover a major portion of the inside surface portion of the at least one sensor tab. The at least one sensor element may be adhesively attached to the inside surface portion of the at least one sensor tab. There may be provided a full surface bonding between the at least one sensor element and the inside surface portion of the at least one sensor tab. In this way, a local deformation of different longitudinal sections of the at least one sensor tab can be measured and detected by the at least one sensor element.

According to a further example the at least one sensor element comprises a strain gauge. A strain gauge is configured to generate or to modify an electrical signal being indicative of a tensile or compressive load present to the strain gauge. As the at least one sensor tab is deformed radially inwardly, the inside surface portion thereof is subject to a bending. In an initial and unbiased configuration the inside surface portion of the at least one sensor tab may be even or straight shaped. As the at least one sensor tab is subject to a radially inwardly directed mechanical load, it may deform towards a certain radius of curvature that is detectable and/or quantitatively measurable by the strain gauge. Alternatively, the inside surface portion of the at least one sensor tab may exhibit a well-defined radius of curvature in the unbiased state. As the sensor tab is subject to a mechanical load, the radius of curvature of the inside surface portion may be subject to a significant change that is detectable and quantitatively measurable by the strain gauge.

According to a further example the body comprises a channel extending into a proximal end of the tubular portion. The channel may be located in a radial center of the body. It may extend parallel to a central axis of the body. The channel may form a hollow structure extending longitudinally through or into the body. The at least one sensor element is connected to at least one wire. The at least one wire extends into the channel. Depending on the specific type of sensor element, the sensor element may even be connected with two separate wires. With such examples both wires extend from the at least one sensor element into the channel.

A microprocessor or a measurement circuit to determine or to measure a degree of mechanical deformation of the at least one sensor tab may be located inside the tubular portion of the elongated body. Alternatively, the measurement electronics, such as a microprocessor or a measurement circuit may be located remote of the measurement probe.

Then and according to a further example the channel extends from the proximal end of the tubular portion towards a distal end of the body. The channel is hollow and may extend in longitudinal direction through the entire body of the measurement probe. In this way, the at least one wire connected to the at least one sensor element at the proximal end of the body may extend all through the channel and may exit the channel at a distal end of the body. Moreover, that at least one wire or a pair of wires may be bunched or bundled to form a cable. In this way, only one elongated cable will extend or protrude from the distal end of the channel at the distal end of the elongated body. With examples comprising a plurality of sensor tabs, each of which equipped with at least one sensor element, the sensor elements may be each provided with at least one or with at least two wires. All wires of all sensor tabs or sensor elements may be bunched or bundled into a single cable extending through the channel.

According to a further example the measurement probe comprises a strain relief clamp that is arranged inside the channel. The at least one wire, numerous wires and/or an optional cable bunching the plurality of wires extends through the strain relief clamp. In this way, the cable or the at least one wire is fixed to the channel and/or to the elongated body. In this way it can be effectively avoided, that any tensile force is transmitted via the at least one wire or the cable from outside the measurement probe towards and into the at least one sensor element. The strain relief clamp prevents that a tensile force is applied to the at least one sensor tab via the at least one wire or cable.

With a further example the measuring probe also comprises a fastening plate detachably fixable to an outside surface of the tubular portion of the measurement probe. The fastening plate comprises one of a circumferential width and a longitudinal length. The circumferential width may match with a tangential width of a window of the cartridge holder. The longitudinal length may match with a longitudinal length of the window of the cartridge holder. If the fastening plate has an outer circumferential width that matches with an inner circumferential width of a window of the cartridge holder, the fastening plate can be assembled inside the window of the cartridge holder free of slack or free of geometric tolerances with regard to the circumferential or tangential direction.

The fastening plate is further fixable to an outside surface of the tubular portion. When fixed to the tubular portion of the elongated body and when accurately fitted into the window of the cartridge holder, the measurement probe can be rotationally fixed to the cartridge holder with regard to the longitudinal or central axis as an axis of rotation. The same is valid for the longitudinal length of the fastening plate. If the longitudinal length of the fastening plate matches with the longitudinal length of the window of the cartridge holder an axial or longitudinal fixing of the measurement probe inside the cartridge holder can be attained.

In another example the measurement probe comprises at least a second sensor tab and at least a second sensor element mechanically connected to the second sensor tab. Also the second sensor tab is arranged on or integrated into the elongated body and comprises an outside surface portion, an inside surface portion and an outer abutment section. The outer abutment section of the second sensor tab is also configured to abut with an inside of a sidewall of a cartridge holder. Like the at least one sensor tab the second sensor tab is also deformable in a radial direction. The second sensor tab may be identically shaped compared to the at least one sensor tab. In particular, the at least one sensor tab and the second sensor tab are arranged concentrically with regard to a central axis of the body. The measurement probe is by no way limited to only two sensor tabs. It may be equipped with three, four, five, six or even more sensor tabs concentrically arranged with regard to the central axis of the body.

Numerous sensor tabs may be equidistantly or equiangularly arranged along the outside circumference of the elongated body. The sensor tabs may all have equal length in longitudinal direction and may have an identical shape. They may be identically fastened to the elongated body. In particular, all sensor tabs and sensor elements may protrude from a proximal end of the tubular portion of the elongated body.

The angular separation between numerous sensor tabs and sensor elements may be in conformity to mutually corresponding fasteners of the cartridge holder and the body of the injection device. If numerous fasteners of the body and the cartridge holder are equidistantly or equiangularly arranged this applies as well to the respective sensor tabs and sensor elements. It is intended that the sensor tabs are located at the same circumferential and axial position as the mutually corresponding fasteners of the body and the cartridge holder of the injection device. Hence, a geometric pattern of multiple sensor tabs and sensor element on the measurement probe matches with a geometric pattern of multiple and mutually corresponding fasteners of the body and the cartridge holder.

According to another aspect the disclosure relates to a measurement system comprising an injection device and comprising a measurement probe as described above. The injection device is configured for setting and injecting of a dose of a medicament. The injection device comprises a body and a cartridge holder. The body is configured to accommodate a drive mechanism, wherein the drive mechanism comprises a piston rod that is configured to urge against a bung of a cartridge filled with a liquid medicament. The body of the injection device comprises a receptacle at a distal end. The cartridge holder comprises an insert portion configured for longitudinal insertion into the receptacle. The cartridge holder is connectable to the body by inserting the insert portion in proximal direction into the receptacle at the distal end of the body. The cartridge holder is further configured to accommodate the cartridge therein. The receptacle and the insert portion comprise mutually engaging snap features to connect and to fix the cartridge holder to the body. For instance, the receptacle of the body may comprise radially inwardly protruding snap features or ratchet features to engage with correspondingly-shaped recesses provided on an outside surface of the insert portion of the cartridge holder. The recesses may comprise a through opening extending through the sidewall of the insert portion of the cartridge holder. The recesses are shaped and sized to receive the snap features provided on the inside surface of the receptacle of the body.

According to another example the measurement probe is insertable into the cartridge holder only in one or several predefined orientations relative to the cartridge holder, in which the at least one sensor tab circumferentially and longitudinally overlaps with one of the snap features when the measurement probe is arranged inside the cartridge holder. In particular, the measurement probe and its elongated body may be circular symmetric with regard to the central axis. In principle, the measurement probe is insertable in an arbitrary rotational configuration inside the cartridge holder with regard to the central axis as an axis of rotation. The outside surface of the tubular portion of the body may comprise a fastening feature to engage with a fastener of the fastening plate.

The fastening feature or numerous fastening features may be located at a well-defined circumferential position on the outside surface of the tubular portion. The position of the fastening features may be selected such, that the fastening feature is located inside a window of the cartridge holder that allows attachment of the fastening plate from outside into the window of the cartridge holder and to use the fastener to connect with the fastening feature thereby fixing the fastening plate inside the window of the cartridge holder and to the outside surface of the tubular portion of the body of the measurement probe.

The angular or circumferential distance of that at least one sensor tab relative to the fastening feature matches with a circumferential distance between the window of the cartridge holder and a snap feature of the cartridge holder. In this way only one or several specific rotational states of the measurement probe are defined, in which the measurement probe is fixable to the cartridge holder by making use of the fastening plate. In this selected angular orientation the at least one sensor tab overlaps with the at least one snap feature of the body and/or the cartridge holder of the injection device. In this way, it can be provided that the at least one sensor tab and the corresponding sensor element are located close to the snap features of the interconnection of the body and the cartridge holder thus enabling measuring of a significant mechanical and geometric deformation of the cartridge holder in the course of assembly of the cartridge holder and the body of the injection device.

According to a further aspect the disclosure also relates to a method of measuring a mechanical load during assembly of an injection device. The method comprises the steps of providing of a body of the injection device. The body is configured to accommodate a drive mechanism. The drive mechanism comprises a piston rod configured to urge against a bung of a cartridge filled with a liquid medicament. The body of the injection device comprises a receptacle at a distal end. In a further method step there is provided a cartridge holder that is connectable to the body. The cartridge holder comprises an insert portion configured for longitudinal, hence a proximal insertion into the receptacle of the body. The receptacle and the insert portion comprise mutually engaging snap features to connect and to fix the cartridge holder to the body. The cartridge holder is configured to accommodate the cartridge. In a further method step the measurement probe as described above is inserted into the cartridge holder. Thereafter the cartridge holder with the measurement probe located therein is connected to the body. During this connection step a radial force acting on the measurement probe is measured during the assembly of the cartridge holder and the body.

The method of measuring the mechanical load is particularly executable by a measurement probe in connection with an injection device as described above. Any features, effects and benefits obtainable by the measurement probe, the injection device and by the measurement system equally apply to the method of measuring the mechanical load; and vice versa.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the scope of the disclosure. Further, it is to be noted, that any reference numerals used in the appended claims are not to be construed as limiting the scope of the disclosure.

BRIEF DESCRIPTION OF THE FIGURES

In the following, numerous examples of the container and of an injection device will be described in greater detail by making reference to the drawings, in which.

DETAILED DESCRIPTION

Figure 1:
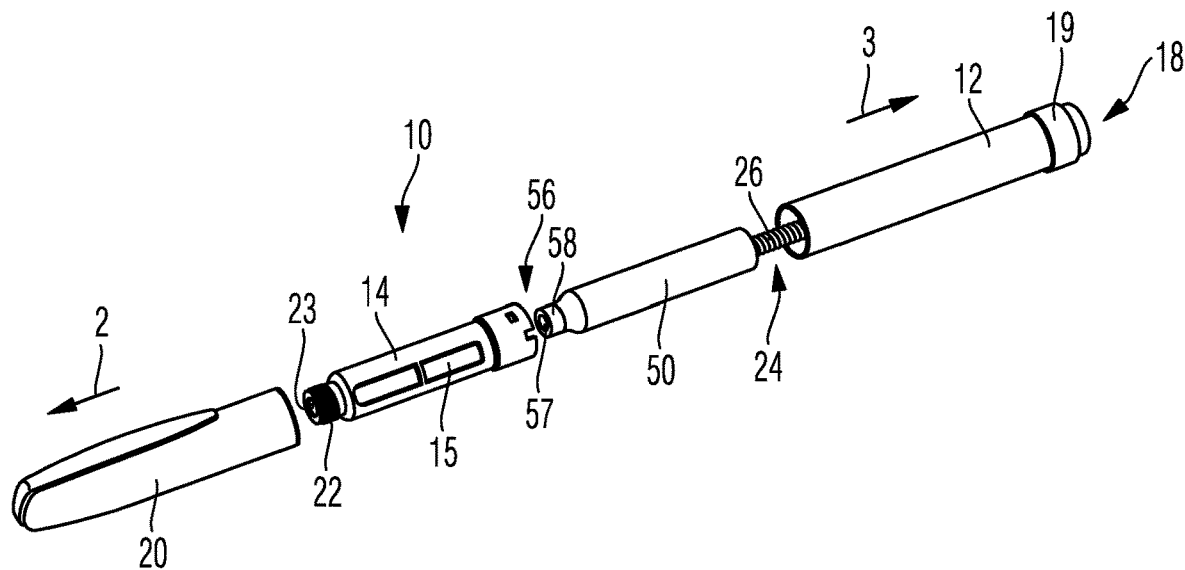
FIG. 1 shows an example of an injection device.

In FIG. 1 an example of an injection device of pen-injector type is illustrated. The injection device 10 comprises a housing having a distal housing component denoted as a cartridge holder 14 and having a proximal housing component denoted as a body 12. At the proximal end of the body 12 there is provided a dose dial 19 configured to set a dose of a medicament to be injected. At the very distal end of the body 12 there is further provided a trigger 18. By depressing the trigger 18 the drive mechanism 24 located inside the body 12 is initiated or enabled to advance a piston rod 26 in distal direction 2 so as to urge a bung 53 of a cartridge 50 in distal direction 2. In this way, a medicament 54 located inside the cartridge 50 can be expelled through a seal 57 at a distal end 56 of the cartridge 50.

Figure 3:
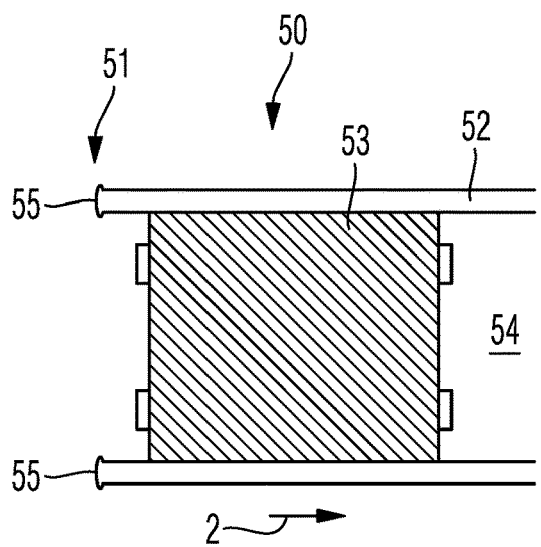
FIG. 3 is a schematic view of the proximal end of the cartridge to be positioned inside the cartridge holder.

The cartridge 50 comprises a proximal end 51 as illustrated in FIG. 3. The proximal end 51 is located opposite to the distal end 56. Towards the proximal direction 3, which is opposite to the distal direction 2, the cartridge 50 is sealed by a bung 53. The bung is of an elastic or flexible material. The bung 53 is typically made of an elastomeric material, such as natural or synthetic rubber. The cartridge 50 comprises a tubular-shaped barrel 52. The bung 53 is located inside the barrel 52. The bung 53 is in sealing engagement with an inside surface of the interior of the sidewall of the barrel 52. In this way the bung 53 is longitudinally or axially displaceable relative to the barrel 52 so as to expel a dose of the medicament from the distal end 56 of the cartridge.

As further indicated in FIG. 3 the very proximal end of the barrel 52 comprises an enamel edge forming a bulged portion 55. Typically, the barrel 52 is made of a vitreous material, such as glass. The enamel edge, hence the radially outwardly bulged portion 55 arises from the manufacturing process of the vitreous barrel 52.

Figure 7:
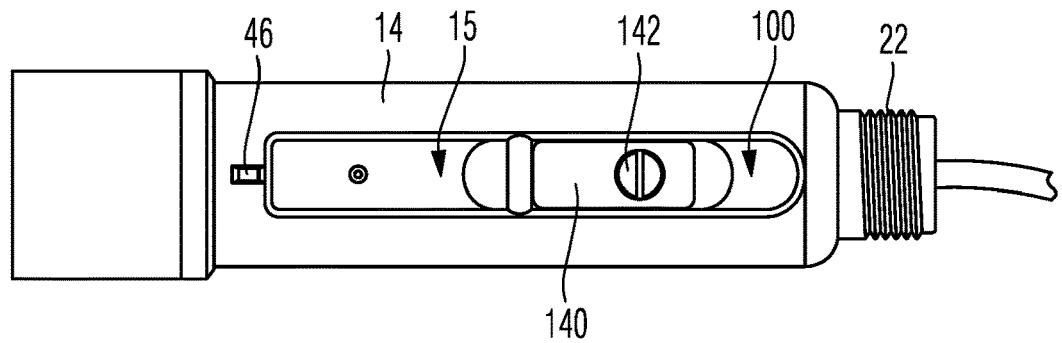
FIG. 7 is a side view of the measurement probe located inside the cartridge holder after assembly of the injection device.

The cartridge 50 is typically to be inserted into the cartridge holder 14. The cartridge holder 14 comprises at least one window 15 formed as a through opening in the sidewall 42 of the cartridge holder 14. A distal end of the cartridge holder 14 is provided with a threaded socket 22. The distal end face of the socket 22 comprises a through opening 23 configured to receive a proximal tipped end of an injection needle to be releasably fastened to the socket 22. The injection device 10 further comprises a protective cap 20 that is to be mounted over the cartridge holder 14. In order to fix the protective cap 20 to the cartridge holder 14 the cartridge holder comprises a snap feature 46 as illustrated in FIG. 7. The radially outwardly protruding snap feature 46 on the outside surface of the tubular section of the cartridge holder 14 is configured to form a snap fit engagement with the protective cap 20, e.g. with an annular groove on an inside surface of the protective cap.

The cartridge 50 is insertable into the cartridge holder 14 from behind, i.e. through a proximal open end of the cartridge holder 14. The cartridge 50 is insertable in distal direction 2 into the proximal end of the cartridge holder 14 until a head of the cartridge 50 is located inside the socket 22. The head of the cartridge 50 is typically provided with a beaded cap 58 for fixing a pierceable seal to the distal end of the cartridge. The pierceable seal serves as a septum pierceable by a double-tipped injection needle.

In the course of assembly the drive mechanism 24 with the piston rod 26 is assembled inside the body 12. The cartridge 50 is assembled inside the cartridge holder 14.

Then the cartridge holder 14 and the body 12 are assembled and interconnected. For this the cartridge holder 14 comprises an insert portion 40 at its proximal end 41. The insert portion 42 is configured for a slidable and proximally directed insertion into a receptacle 30 provided at a distal end of the body 12. The receptacle 30 is delimited or confined in proximal direction 3 by a web 31 extending transversely almost all over the inner cross-section of the body 12. The web 31 comprises a central through opening 36 through which the piston rod 26 extends. The through opening 36 may comprise an inner thread in threaded engagement with the piston rod 26.

There are provided numerous radially inwardly protruding snap features 33 protruding from an inside of the sidewall 32 of the receptacle 30. The snap features 33 each comprise a protrusion 34 with a beveled edge facing in distal direction 2. The insert portion 40 comprises counter snap features 43 configured to engage with the snap features 33 of the body 12 as the insert portion 40 is urged in proximal direction into the receptacle 30. The counter snap features 43 each comprise a recess 44 sized to receive a protrusion 34.

The insert portion 40 is delimited or confined in distal direction 2 by a flange 45 protruding radially outwardly from the outside surface of the sidewall 42 of the cartridge holder 14. A final assembly configuration is reached and the proximally directed inserting motion of the insert portion 40 into the receptacle 30 is delimited either by an axial abutment of the proximal end 41 of the insert portion with the web 31 and/or by an axial abutment of the flange 45 with a distal end face of the sidewall 32 of the body 12.

Figure 2:
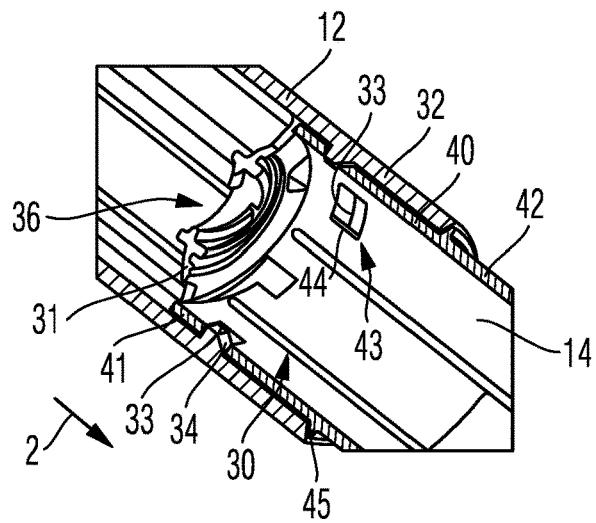
FIG. 2 is a perspective view of the interface of the body and the cartridge holder of the injection device.

In the course of assembly the insert portion 40 and/or the receptacle 30 are subject to a slight mechanical and geometric deformation in radial direction until the mutually corresponding snap features 33 and counter snap features 43 arrive at a final fixing configuration as illustrated in FIG. 2. Since the cartridge holder 14 is precisely shaped for a custom fit arrangement of the cartridge 50 therein, a radially inwardly directed deformation of the sidewall 42 of the cartridge holder 14 may exert a radially inwardly directed pressure onto the barrel 52, especially on the bulged portion 55 of the cartridge 50.

For quantitatively and precisely measuring a mechanical load present on the cartridge 50 there is provided a measurement probe 100 as illustrated in FIGS. 4-10. The measurement probe 100 comprises an elongated body 104 comprising a proximal end 101 and a distal end 102. At the distal end 102 the measurement probe 100 comprises a head portion 110 extending in proximal direction into a radially narrowed neck portion 107. The neck portion 107 transitions in proximal direction 3 into a radially widened shoulder portion 108. Starting from the proximal end of the shoulder portion 108 towards the proximal end 101 the body 104 comprises a somewhat homogeneously shaped tubular portion 106. At the proximal end of the tubular portion 106 there are provided numerous sensor tabs 114, 214. The sensor tabs 114, 214 are integrally formed with the tubular portion 106.

Figure 9:
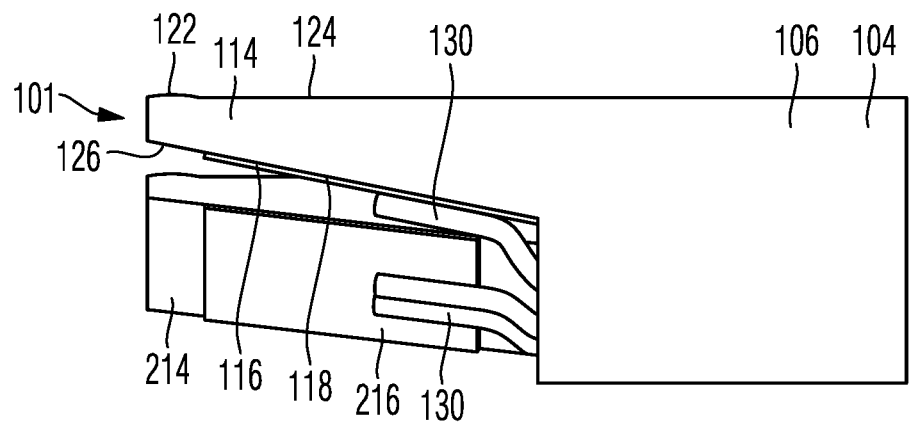
FIG. 9 is an enlarged view of the proximal end of the measurement probe.

The entire measurement probe 100, hence the body 104 may consist of a single piece. The sensor tabs 114, 214 protrude in proximal direction 3 from the proximal end of the tubular portion 106. The tubular portion 106 and the sensor tabs 114, 214 may be integrally formed. The sensor tabs 114, 214 comprise an outside surface portion 124 and an inside surface portion 126 as illustrated in FIG. 9. Moreover, the sensor tab 114 as illustrated in FIG. 9 in greater detail comprises an outer abutment section 122. The outer abutment section 122 comprises an outwardly extending bulged portion having a shape substantially identical or at least similar to the bulged portion 55 of the barrel 52 of the cartridge 50. The shape and position of the outwardly bulged outer abutment section 122 is adapted to the shape and position of the bulged portion 55 of the cartridge 50. The outer diameter and the overall geometry of the body 104 is substantially identical and matches with the outer shape and geometry of the cartridge 50 originally intended to be placed inside the cartridge holder 14.

On the inside surface portion 126 there is further provided at least one sensor element 116. The at least one sensor element 116 is adhesively attached, typically by a full surface bonding to the inside surface portion 126. The at least one sensor element 116 is configured to measure a geometric deformation of the at least one sensor tab 114 in case the sensor tab 114 is subject to a radially directed deformation.

Typically, the sensor element 116 comprises or is a strain gauge 118. The sensor element 116 and hence the strain gauge 118 is connected with at least one wire 130. It may even be connected with two wires so as to generate or to modify an electrical signal in response to a varying mechanical load present to the sensor tab 114, 214.

At least one or two wires 130 are connected to each of the sensor elements 116, 216. The sensor element 216 is connected to the sensor tab 214 and the sensor element 116 is connected to the sensor tab 114. The sensor tabs 114, 214 as well as the respective sensor elements 116, 216 are identically shaped. They are also identically configured so as to provide substantially identical measurement results in case of an identical mechanical load present to the respective sensor tabs 114, 214 and sensor elements 116, 216.

Figure 5:
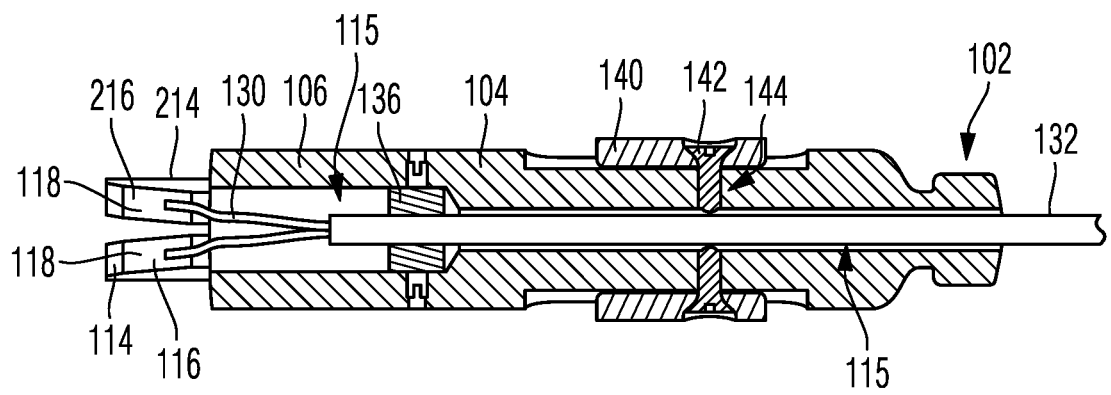
FIG. 5 is a longitudinal cut through the measurement probe according to FIG. 4.
Figure 8:
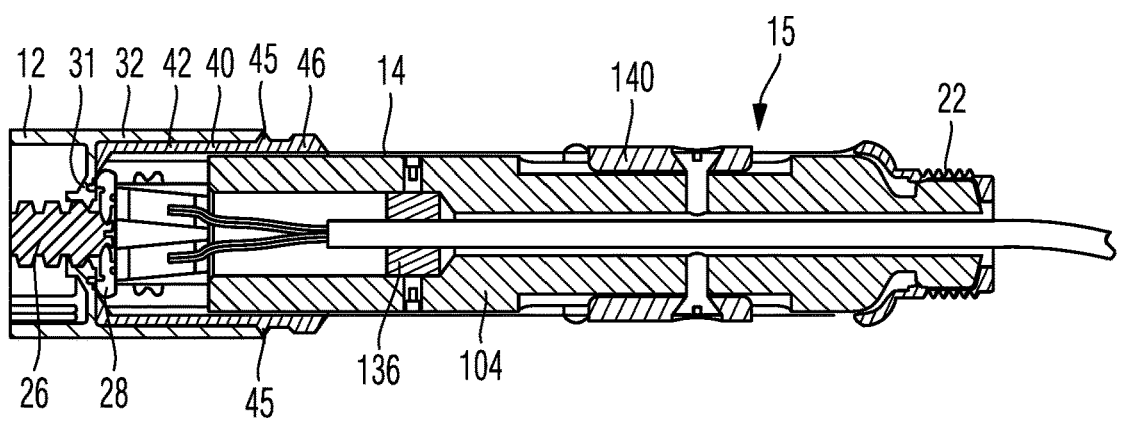
FIG. 8 is a longitudinal cut through the arrangement of FIG. 7.

As further illustrated in FIGS. 5 and 8 there extends a channel 115 through the body 104 in longitudinal direction. The channel 115 coincides with a central axis 105. The channel 115 extends from the proximal end of the body 104 towards and through the distal end 102 of the body 104. The various wires 130 may be bunched to a single cable 132 extending through the channel 115 and protruding from the distal end 102 of the measurement probe 100. The cable 132 may be fixed inside the channel 115 by means of a strain relief clamp 136 as illustrated in FIGS. 5 and 8.

As illustrated in greater detail in FIG. 9 the outside surface portion 124 of the sensor tabs 114, 214 is flush and parallel to an outside surface of the tubular portion 106 of the body 104. The inside surface portion 126 is somehow inclined or slanted with regard to the central axis 105 as well as with regard to the outside surface portion 124. The outside surface portion 124 is aligned parallel to the central axis 105. The inside surface portion 126 is inclined radially inwardly towards the distal end 102 of the measurement probe. In this way and towards the proximal end 101 the thickness of the sidewall of the sensor tabs 114, 214 gradually decreases.

Figure 6:
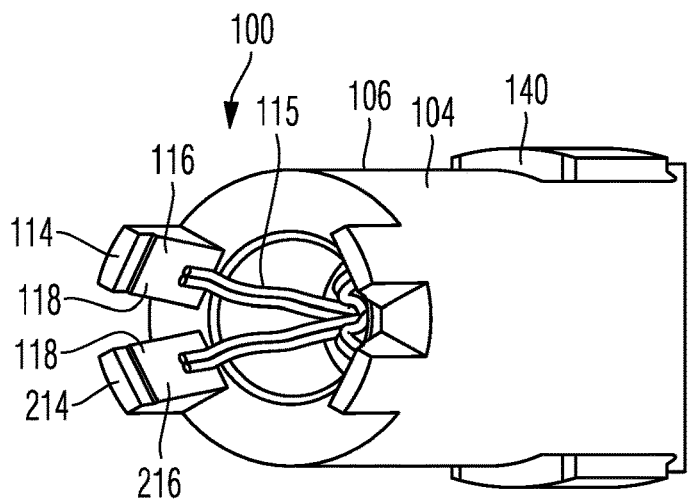
FIG. 6 is a perspective view of the proximal end of the measurement probe.

At the proximal end 101 the thickness of the sensor tabs 114, 214 is at a minimum. The sensor elements 116 cover a major portion of the surface of the inside surface portion 126. As illustrated in FIG. 6, the sensor tabs 114, 214 are of substantial rectangular shape. Hence, the circumferential width of the sensor tabs 114, 214 is constant in longitudinal direction. The decrease of the sidewall thickness of the sensor tabs 114, 214 towards the proximal end is beneficial to provide a well-defined deformation in response to a mechanical load acting radially inwardly onto the outer abutment section 122. In this way and since the sensor tabs 114, 214 protrude proximally from the proximal end of the tubular portion 106 they may exhibit a well-defined elastic deformation behavior in response to a radially inwardly directed force effect emanating from and during the formation of a clip joint between the cartridge holder 14 and the body 12.

Figure 4:
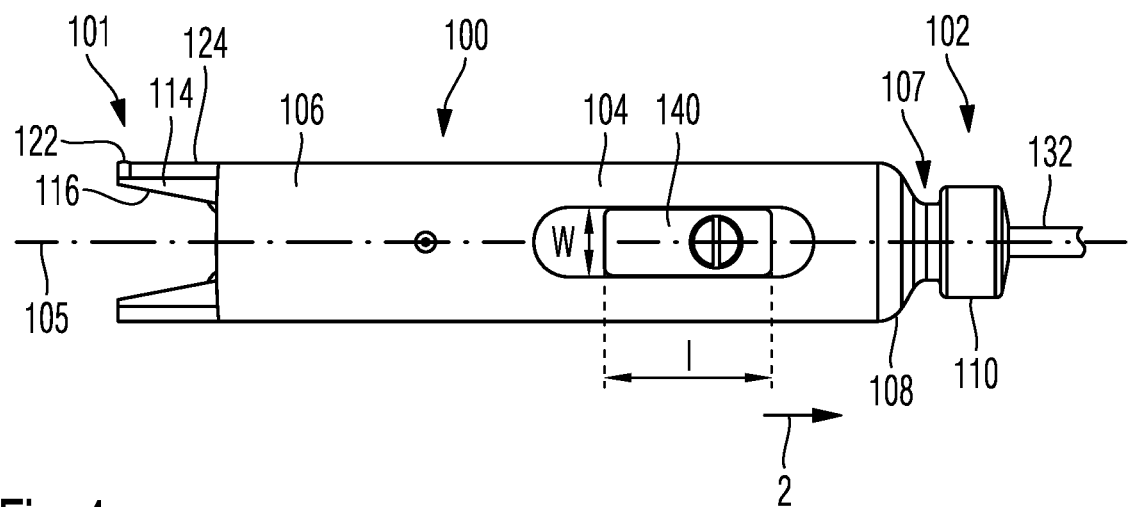
FIG. 4 is a side view of the measurement probe.

As illustrated further in FIGS. 4 and 5 there is provided a fastening plate 140 to be fastened and assembled to an outside surface of the tubular portion 106. For this, the body 104 comprises a fastening feature 104 to engage with a fastener 142. The fastener 142 intersecting the fastening plate 140 and engaging the fastening feature 144 of the body 104 serves to fix the fastening plate 140 to the outside surface of the body 104. The fastening plate as illustrated in FIG. 4 comprises a longitudinal length l and a circumferential width w. The circumferential width w matches with a circumferential width of the window 15 of the cartridge holder 14. In this way and as illustrated in FIG. 7, the fastening plate 140 can be assembled from outside the cartridge holder 14 into the window 15 in a custom fit. Then, the fastener, e.g. in form of a screw with an outer thread can be screwed into the fastening feature 144, e.g provided in form of a threaded hole of the body 104. In this way, the fastening plate 140 is rigidly fastened to the body 104 and the body 104 is hence prevented from rotating relative to the cartridge holder 14 with the central axis 105 as an axis of rotation.

Figure 10:
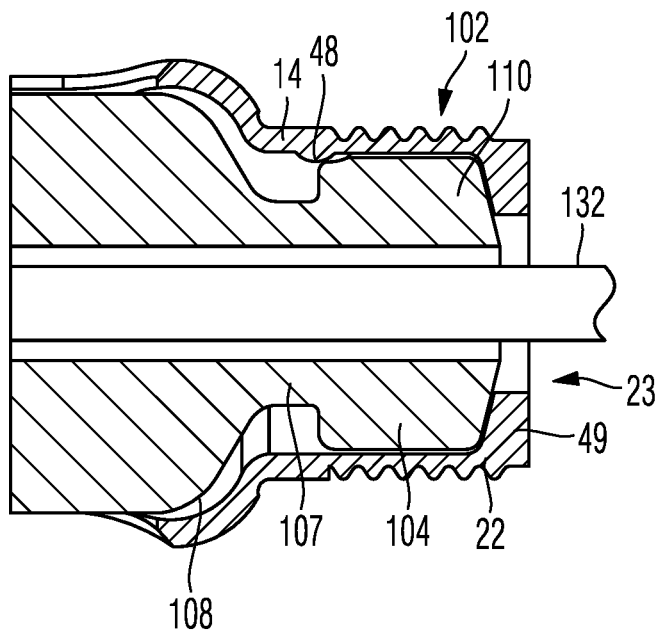
FIG. 10 is an enlarged view of the distal portions of the measurement probe and of the cartridge holder and FIG. 11 is a flowchart of the method of measuring the mechanical load during assembly of the injection device.

In another example and when the longitudinal length l of the fastening plate 140 matches the longitudinal length of the window 150 also an axial fixing of the body 104 to the cartridge holder 14 can be attained. In the present example the cartridge holder 14 comprises a radially inwardly extending protrusion 48 on the inside of the threaded socket 22 as illustrated in FIG. 10. The protrusion 48 is configured to snap under the head portion 110 of the body 104. The distal end face of the head portion 110 is in axial abutment with a radially inwardly directed flange 49 radially confining the through opening 23 at the distal end face of the cartridge holder 14. In this way, and by the form fit engagement of the head portion 110 with the flange 49 and the protrusion 48 the measurement probe 100 can be axially fixed inside the cartridge holder 14.

The arrangement of the sensor tabs 114, 214 with respective sensor elements 116, 216 is configured such that the degree of radial deformation of the sensor tab 114, 214 is unequivocally and unambiguously assigned to a force effect. The greater the force or the mechanical impact applied to the at least one sensor tab 114, 214 the greater will be the radial deformation of the respective sensor tab 114, 214. A degree or a magnitude of mechanical and geometric deformation of the sensor tabs 114, 214 is or are detectable and quantitatively measurable by the sensor elements 116, 216. Respective electric measurement signals may be calibrated and gauged. Hence, the measurement probe and each of its individual sensor tabs 114, 214 may be subject to a calibration process, wherein a force of known strength is applied to each sensor tab 114, 214 and a respective measurement signal is recorded in a respective calibration table. Later on and under real conditions inside the injection device 10 the electrical signal obtainable from the sensor element 116, 216 is a direct indication and measure of a force actually applied to the respective sensor tab 114, 214.

As it is apparent from FIG. 2, the mutually corresponding snap features 33 and counter snap features 43 are not equidistantly arranged along the circumference of the receptacle 30 and of the insert portion 40. With the presently illustrated example there are two pairs of oppositely located snap features 33 and two pairs of correspondingly arranged counter snap features 43. For each snap feature and counter snap feature combination there is provided one sensor tab 114, 214. As illustrated in FIG. 6 there are provided altogether four sensor tabs 114, 214 at the proximal end of the tubular portion 106 of the body 104. Typically, each sensor tab 114, 214 is arranged in an overlapping configuration with a snap feature 33 and a counter snap feature 43 so as to enable a rather precise force measurement as the body 12 and the cartridge holder 14 are interconnected.

The counter snap features 43 are in a well-defined circumferential distance with regard to the window 15 of the cartridge holder 14. Accordingly, the fastening feature 144 or the fastening plate 140 will be in the same angular or circumferential relation with the sensor tabs 114, 214. In this way, the measurement probe 100 can be inserted into the cartridge holder 14 only in one or two dedicated rotational orientations with regard to the central axis 105. In each of these allowable and supported angular orientations with regard to the central axis 105 the sensor tabs 114, 214 are in an overlapping arrangement with the snap features 33 and counter snap features 43.

Figure 11:
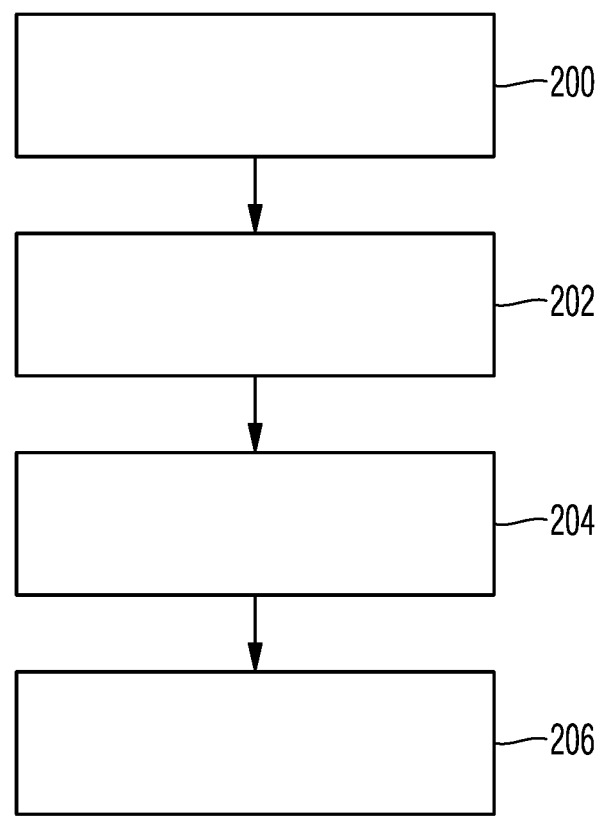

In FIG. 11 a flowchart of the method of measuring a mechanical load during assembly of the injection device 10 is given. In a first step 200 a body 12 of the injection device 10 is provided.

The body is configured to accommodate the drive mechanism 24 having a piston rod 26 that is configured to urge against the bung 53 of the cartridge 50. As illustrated in FIG. 8 the piston rod 26 is typically equipped with a radially widened pressure piece 28 or bearing at a distal end which is configured to abut with a proximal side of the bung 53. The body 12 comprises the above mentioned receptacle 30 at a distal end. In step 202 the cartridge holder 14 is provided which is connectable to the body 12. The cartridge holder 14 is configured to accommodate the cartridge 50. The cartridge holder 14 comprises an insert portion 40 that is configured for longitudinal insertion into the receptacle 30. The receptacle 30 and the insert portion 40 comprise mutually engaging snap features 33, 43 to connect and to fix the cartridge holder 14 to the body 12.

In step 204 the measurement probe 100 as described above is inserted into the cartridge holder from behind. For this, the cable 132 protruding from the distal end 102 of the measurement probe 100 is threaded from the proximal end of the cartridge holder 14 through the distal through opening 23. Then the measurement probe 100 is inserted into the cartridge holder 14 into the proximal open end of the cartridge holder in distal direction 2. After insertion of the measurement probe 100 into the cartridge holder 14 the cartridge holder 14 is connected to the body 12 in step 206. During this connection and during insertion of the insert portion 40 into the receptacle 30 the radial force acting on the measurement probe 100 is measured by the elastically deformable sensor tabs 114, 214 and the associated sensor elements 116, 216, respectively.

LIST OF REFERENCE NUMBERS 2 distal direction
3 proximal direction
10 injection device
12 body
14 cartridge holder
15 window
18 trigger
19 dose dial
20 protective cap
22 threaded socket
23 through opening 24 drive mechanism
26 piston rod
28 pressure piece
30 receptacle
31 web
32 sidewall
33 snap feature
34 protrusion
36 through opening
40 insert portion
41 proximal end
42 sidewall
43 counter snap feature
44 recess
45 flange
46 snap feature
48 protrusion
49 flange
50 cartridge
51 proximal end
52 barrel
53 bung
54 medicament
55 bulged portion
56 distal end
57 seal
58 beaded cap
100 measurement probe
101 proximal end
102 distal end
104 body
105 central axis
106 tubular portion
107 neck portion
108 shoulder portion
110 head portion
114 sensor tab
115 channel
116 sensor element
118 strain gauge
122 abutment section
124 outside surface portion
126 inside surface portion
130 wire
132 cable
136 strain relief clamp
140 fastening plate
142 fastener
144 fastening feature
214 sensor tab
216 sensor element

The invention claimed is:

1. A measurement probe for measuring a mechanical load, the measurement probe comprising:
an elongated body comprising a tubular portion configured for insertion into a cartridge holder of an injection device;
at least one sensor tab arranged on or integrated into the elongated body, wherein the at least one sensor tab comprises an outside surface portion, an inside surface portion and an outer abutment section, wherein the outer abutment section is configured to abut with an inside of a sidewall of the cartridge holder and wherein the at least one sensor tab is deformable in a radial direction; and
at least one sensor element mechanically connected to the at least one sensor tab and configured to measure a deformation of the at least one sensor tab.

2. The measurement probe of claim 1, wherein the at least one sensor tab is elastically deformable and is integrally formed with the elongated body.

3. The measurement probe of claim 1, wherein the at least one sensor tab is arranged at a proximal end of the body and protrudes proximally from the tubular portion.

4. The measurement probe of claim 1, wherein the outside surface portion of the at least one sensor tab is flush with an outside surface of the tubular portion as seen in longitudinal direction.

5. The measurement probe of claim 1, wherein the abutment section is located at a proximal end of the at least one sensor tab.

6. The measurement probe of claim 1, wherein the abutment section bulges outwardly from the outside surface portion.

7. The measurement probe of claim 3, wherein the at least one sensor tab comprises a narrowing radial thickness towards the proximal end.

8. The measurement probe of claim 1, wherein the inside surface portion of the at least one sensor tab is inclined inwardly towards a distal end of the body with regard to a central axis of the body.

9. The measurement probe of claim 1, wherein the at least one sensor element is fixed on the inside surface portion of the at least one sensor tab.

10. The measurement probe of claim 1, wherein the at least one sensor element comprises a strain gauge.

11. The measurement probe of claim 1, further comprising a fastening plate detachably fixable to an outside surface of the tubular portion, wherein the fastening plate comprises one of a circumferential width matching a tangential width of a window of the cartridge holder and a longitudinal length matching a longitudinal length of the window.

12. The measurement probe of claim 1 comprising at least a second sensor tab and at least a second sensor element mechanically connected to the second sensor tab.

13. The measurement probe according to claim 12, wherein the second sensor element is configured to measure a deformation of the second sensor tab, wherein the at least one sensor tab and the second sensor tab are arranged concentrically with regards to a central axis of the body.

14. A system comprising:
a measurement probe comprising:
an elongated body comprising a tubular portion configured for insertion into a cartridge holder of an injection device,
at least one sensor tab arranged on or integrated into the elongated body, wherein the at least one sensor tab comprises an outside surface portion, an inside surface portion, and an outer abutment section, wherein the outer abutment section is configured to abut with an inside of a sidewall of the cartridge holder and wherein the at least one sensor tab is deformable in a radial direction, and
at least one sensor element mechanically connected to the at least one sensor tab and configured to measure a deformation of the at least one sensor tab; and
an injection device configured for setting and injecting of a dose of a medicament, the injection device comprising:
a body to accommodate a drive mechanism, the drive mechanism comprising a piston rod configured to urge against a bung of a cartridge filled with a liquid medicament, wherein the body comprises a receptacle at a distal end, and a cartridge holder connectable to the body and configured to accommodate the cartridge, wherein the cartridge holder comprises an insert portion configured for longitudinal insertion into the receptacle, wherein the receptacle and the insert portion comprise mutually engaging snap features to connect and to fix the cartridge holder to the body.

15. The system of claim 14, wherein the measurement probe is insertable into the cartridge holder only in one or more predefined orientations relative to the cartridge holder, in which the at least one sensor tab circumferentially and longitudinally overlaps with one of the snap features when the measurement probe is arranged inside the cartridge holder.

16. The system of claim 14, wherein the at least one sensor tab is elastically deformable and is integrally formed with the elongated body.

17. The system of claim 14, wherein the at least one sensor tab is arranged at a proximal end of the body and protrudes proximally from the tubular portion.

18. The system of claim 14, wherein the outside surface portion of the at least one sensor tab is flush with an outside surface of the tubular portion as seen in longitudinal direction.

19. A method of measuring a mechanical load during assembly of an injection device, the injection device comprising a body to accommodate a drive mechanism and a cartridge holder connectable to the body and configured to accommodate a cartridge, the method comprising:

receiving at least a first signal from at least one sensor element mechanically connected to at least one sensor tab, the at least one sensor element being configured to measure a deformation of the at least one sensor tab, the sensor tab being arranged on or integrated into an elongated body of a measurement probe inserted into the cartridge holder of the injection device, wherein the at least one sensor tab comprises an outside surface portion, an inside surface portion, and an outer abutment section, wherein the outer abutment section is configured to abut with an inside of a sidewall of the cartridge holder and wherein the at least one sensor tab is deformable in a radial direction; and determining a radial force acting on the measurement probe during the assembly of the cartridge holder and the body of the injection device on the basis of the at least first signal, wherein the first signal indicating a deformation of the first sensor tab.

20. The method of claim 19, further comprising:

receiving at least a second signal from at least a second sensor element mechanically connected to at least a second sensor tab, the second sensor element being configured to measure a deformation of the at least second sensor tab, the second signal indicating a deformation of the second sensor tab, wherein the at least one sensor tab and the second sensor tab are arranged concentrically with regards to a central axis of the injection device.

* * * * *